United States Patent [19]

Faisandier

[11] Patent Number: 4,695,955
[45] Date of Patent: Sep. 22, 1987

[54] ELECTRONIC DEVICE PROVIDING A UNIVERSAL INTERFACE BETWEEN SENSORS AND AN ACQUISITION AND PROCESSING UNIT OF THE SIGNALS ORIGINATING FROM SAID SENSORS

[75] Inventor: Yves Faisandier, Paris, France

[73] Assignee: A2F, Paris, France

[21] Appl. No.: 686,450

[22] Filed: Dec. 26, 1984

[30] Foreign Application Priority Data

Dec. 26, 1983 [FR] France .................... 83 20770

[51] Int. Cl.$^4$ ........................................ G06F 13/00
[52] U.S. Cl. .............................. 364/413; 364/422; 364/571; 128/419 R
[58] Field of Search ... 364/413, 422, 571, 200 MS File, 364/900 MS File; 128/419 R

[56] References Cited

U.S. PATENT DOCUMENTS

| | | | |
|---|---|---|---|
| 4,355,310 | 10/1982 | Belaigues et al. | 364/422 X |
| 4,423,408 | 12/1983 | Place | 364/571 X |
| 4,545,380 | 10/1985 | Schoreppel | 128/419 P |
| 4,562,554 | 12/1985 | Strixrud et al. | 364/557 X |
| 4,589,088 | 5/1986 | Place | 364/900 |

Primary Examiner—Jerry Smith
Assistant Examiner—Charles B. Meyer
Attorney, Agent, or Firm—Wenderoth, Lind & Ponack

[57] ABSTRACT

An electronic device provides a universal interface between sensors and an acquisition and processing system of the signals originating from the sensors, wherein the various sensors are connected to standardized terminals (1 . . . 6), appearing all identical to the user and comprising energization (M) and amplifying (A, $A_p$) elements, capable of being adapted to said sensors, and identification means ($R_{ECG}$, $R_{PRE}$) for automatically recognizing the sensor present in the terminal, so as to allow programming the signal amplification, energization and processing elements.

10 Claims, 5 Drawing Figures

ELECTRONIC DEVICE PROVIDING A UNIVERSAL INTERFACE BETWEEN SENSORS AND AN ACQUISITION AND PROCESSING UNIT OF THE SIGNALS ORIGINATING FROM SAID SENSORS

FIELD OF THE INVENTION

This invention relates to a device devised so as to allow connecting, in a signal acquisition and processing system, a plurality of sensors on standardized sockets or terminals appearing as identical to the user.

Notably, this invention can be applied, without this application being in any way limiting, to providing a universal interface between medical sensors (such as for example: electrocardiographic signal sensors, breathing, temperature, blood-pressure, pulse sensors, etc. ... ) and a signal processing apparatus such as a bedside monitor, a catheter sounding bay, etc. ...

BACKGROUND OF THE INVENTION

For the present, the acquisition and processing units for biological signals are made of several interfaces connected to a centralizing system for the management of the alarms and the visualization of the signals or data resulting from the processing of the signals.

FIG. 1 of the accompanying drawings is a block-diagram illustrating an embodiment of such a system according to the present state of the art. To each sensor (electrocardiographic signal sensor-electrodes E; blood-pressure sensor $C_P$; temperature sensor $C_T$, etc. ..) is affected an interface, respectively $I_{ECG}, I_P, I_T, \ldots I_n$, and the interfaces are connected to the centralizing system which is in turn connected for example to a visualization display screen V.

In this known system, each interface is specific to a particular sensor and includes electronic elements providing the amplification, the insulation and various processings particular to the sensor in question. Said sensor is connected to said interface via a terminal provided with a fool-proof device to avoid connection errors when using several interfaces on the same unit.

In order to make such acquisition and processing units more flexible in use, the manufacturers have integrated on some systems interchangeable modules: an acquisition unit comprising four channels for example can be configured to the requirements of the user as a function of the needs of the patient under supervision.

This relatively stabilized technique does not only offer advantages. Indeed:

(1) It is very costly: the manufacture of the module acquisition system is more complex than a frozen system (also called "compact"). To it have to be integrated:
  the mechanical elements ensuring the fixation of the modules,
  the connectors providing the connection between the system and each module,
  a very flexible management system adapted for displaying on the screen the data relative to each possible module.

Moreover, the user has to have at his disposal a large number of modules for being able to use his systems in an optimal way.

(2) The module housings are dust-traps:

Each acquisition system is seldom loaded with all its modules. The empty compartments provide an access to the connection system, to support rails difficult to clean and possibly to sterilze. Such comparments are seldom closed in practice and they become dust-traps, badly accepted in medical environments.

(3) The management of the modules by the department using them is sometimes difficult since some particular modules may be insufficient in number if several patients are suffering from a pathology necessitating the use of one of said modules.

OBJECTS AND SUMMARY OF THE INVENTION

The object of the invention is to provide the same advantages of said modular systems without their disadvantages and aims at making the use of the acquisition systems considerably simpler.

To this effect, the invention relates to an electronic device allowing, on a signal acquisition and processing system, connecting directly a plurality of sensors, said device being characterized in that the various sensors are connected to standardized terminals, all appearing as identical to the user and comprising a sensor identification means and energization and amplifying elements which are adaptable to said sensors.

BRIEF DESCRIPTION OF DRAWINGS

Other features and advantages of this invention will become more apparent from the hereafter description, with reference to the accompanying drawings illustrating one embodiment thereof, without any limiting character.

In the drawings.

DETAILED DESCRIPTION OF EMBODIMENT

Figure 1:
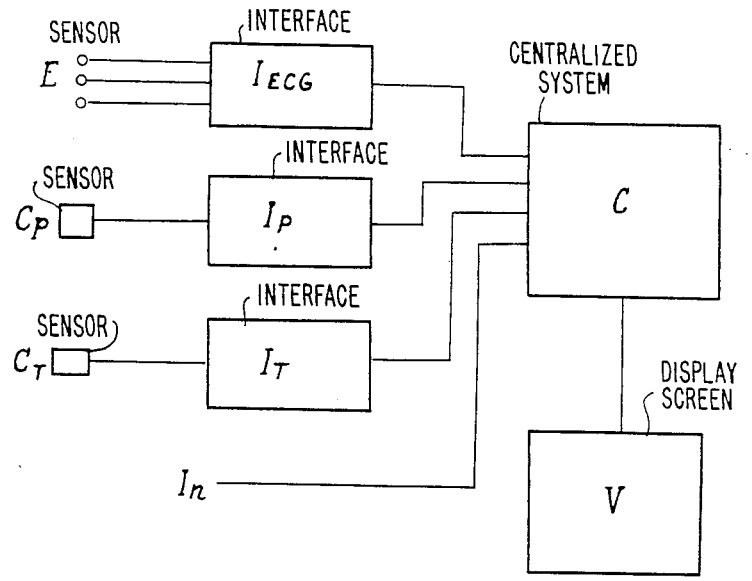
FIG. 1 is a block-diagram illustrating the prior art discussed hereabove.

It will be appreciated that the invention consists in using the same connector, whatever the type of sensor which has to be connected to the signal acquisition and processing system. Thus, an acquisition system including for example four channels presents, according to the invention, four terminals of absolutely identical aspect. The user has simply to connect to sensor or sensors of his choice to one of the terminals in order that the unit operates with this or these sensors. Thus is provided a "universal terminal". In order to provide such a terminal, it is necessary to know the various types of interfaces allowing the connection of all the sensors used. Thus, for a medical application, the use of the following sensors can be considered:
  electrocardiographic signals sensor (ECG),
  breathing sensor,
  blood-pressure sensor,
  temperature sensor,
  pulse sensor,
  possibly sensors of gases in the blood, of the heart delivery rate, etc. ...

The signal particular to each sensor is processed, either within the system or by a locak processor, by using modules, for example of the logical type, set in function as required. The part played by the interface is therefore limited to the generation of a signal reflecting correctly the activity of the sensor.

In this particular application, which of course has no limiting character, two types of interfaces are necessary:

an ECG-breathing interface: the elcrtodes whose function is to detect electrocardiographic signals serve also to measure the trans-thoracic impedance reflecting the breathing movements;

an interface for a "Wheatstone bridge", applicable to all the other sensors. Passive components, placed in the terminal of the sensor and/or of the programmable-gain amplifiers, allow taking account of the sensitivity devergences of a type of sensor with respect to another.

These two types of interfaces are substantially different due to the fact that one of them (ECG-brathing) amplifies directly the signals emitted by the heart, and that the other energizes with an alternating signal the Wheatstone bridge the differential value of which is amplified and demodulated. In fact, it is possible to gather said two interfaces as a single electronic chain comprising programmable elements and notably a switchable demodulator set in function by the Wheatstone bridge.

Thus, the universal interface concept according to the invention is put in practice.

In order to bring into effect said universal interfaces, the system has to possess a means for automatically recognizing the sensor which is present in the terminal, in order to program the amplifying elements, the processing mode and the presentation of the outgoing signal. Said means may be provided for example by using a passive component (resistor) integrator into the sensor's terminal, and the value of which is read by the system: each sensor type is thus coded by a given value of the resistor. Other means can also be used, such as notably: the measurement of the current consumed by the sensor, a mask interposed in front of a photoelectric cell, an active component providing a digital code. . . .

For obtaining certain particular functions, the here-above described chain can become relatively complex. Where said function can be present only once with a patient under supervision, it is sufficient to dispose of the elements adapted for providing said function and to be able to switch over to any chain, at a point correctly adapted. However, if local processors are used, it is possible to integrate a great number of functions in the chain as such. The switching previously evoked then becoms unnecessary.

An embodiment of a universal terminal according to this invention will now be described.

Such a system comprises substantially the following circuits:

I—one or several chains forming the "universal" interface;

II—an insulation circuit common to the various chains and providing on the one hand the insulation of said chains with respect to the rest of the system and on the other hand the transfer of the output levels of the amplifying elements, and the transfer of the controls originating from the system.

III—the circuits providing the logical functions allowing the management of the chain assembly.

I—Chain providing the universal interface

Figure 2:
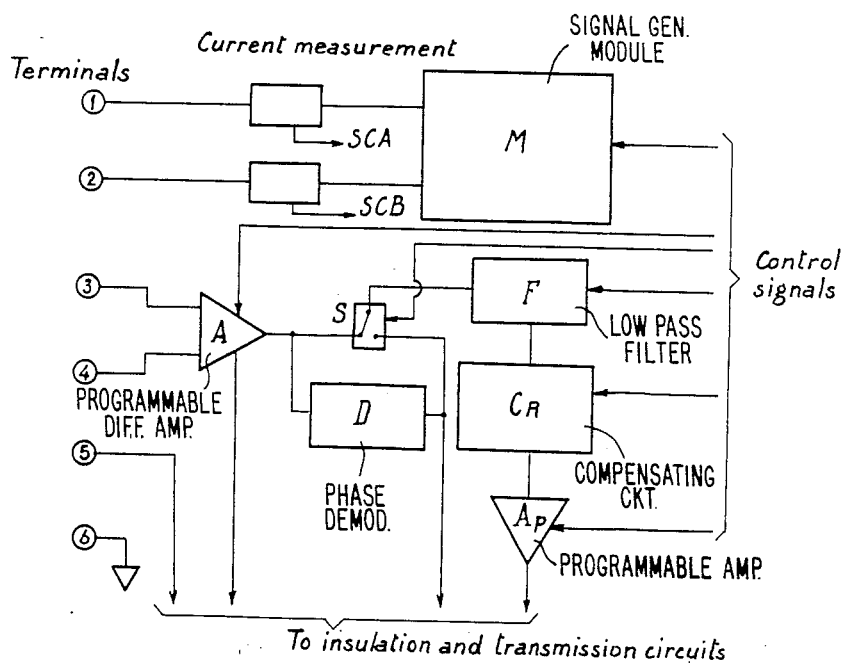
FIG. 2 is an illustration in the form of a block-diagram of an embodiment of a universal interface according to the invention.

It comprises two distinct elements (FIG. 2):

a "generator of graded signal" M module, adapted for providing two voltage graded signals SCA, SCB, of programmable or fixed shape, for example square. The current flowing in each leg is measured. By way of example, one can chose two square signals of 0 V–5 V in opposition of phase of 10 kHz frequency.

an amplification chain comprising the following elements:

a programmable differential amplifier A, receiving the signals from the sensor, differentiating them and amplifying them. It includes a second output corresponding to the middle point of the amplifier which can be switched to a line common to the chains. This allows applying a standard technique in electrocardiography the function of which is to improve the common mode rejection: the level of said middle point is always brought back to a zero voltage with the assistance of an integrator and of a so-called "active earth" electrode;

a switchable, phase demodulator D, the function of which is to demodulate the alternating signals of small amplitude incoming from a Wheatstone bridge;

a 0 corrector or compensating circuit, $C_R$, the function of which is to correct the "0" displacement or shift of a sensor, or to simulate a high pass filter (this being the case of the ECG or of the pulse for example). It allows adding a continuous level to the signal, with dynamics which can reach several hundreds of times the signal;

a programmable amplifier $A_p$ the function of which is to bring the signal to a high enough level;

a low pass filter F eliminating the HF contents present in the signal, representing the inter-electrode impendance in the case of an ECG, or due to the demodulation in the case of the Wheatstone bridge. Preferably, it is placed after the demodulator switch so that the HF does not to interfere with the following stages.

Said elements can be provided in various ways: analog or digital components, or processor(s) including logical modules.

The input terminal includes six pins. Each of said sensors is connected by a terminal comprising some passive elements providing functions particular to the sensor and means for recognizing it.

Figure 3:
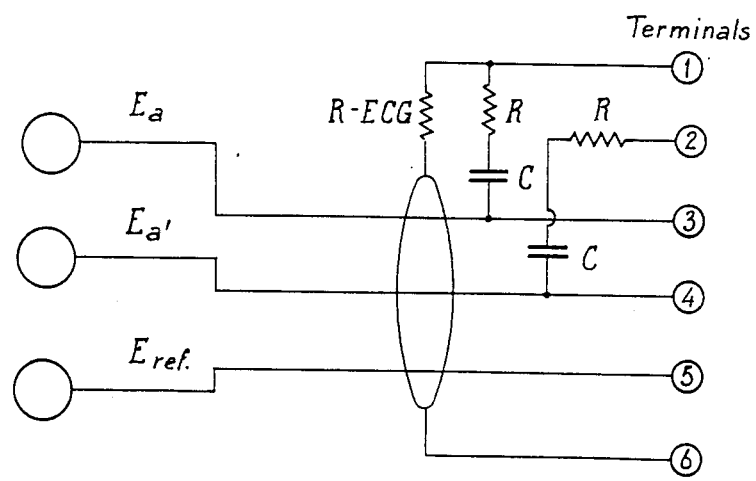
FIG. 3 shows an electrocardiographic signal sensor.

For each sensor in consideration, the interface operates in a particular manner:

(a) For the electrocardiographic signal sensor ECG (FIG. 3), the two active electrodes $E_a$, $E_{a'}$ are connected to the inputs of amplifier A. The square signals are applied via two RC networks (present in the terminal) to these inputs, in order to have a small alternating current flowing between said electrodes (measurement of the inter-electrode impendence in order to detect the disconnection of one of them). The reference electrode $E_{ref}$ is connected on a line common to all the terminals, in liaison with the integrator (active ground). The system connects automatically the input of the integrator to the first existing ECG channel. The alternating signal representing the inter-electrode impedance is demodulated and collected via a switch on a common line of the chains. When several ECG channels are used, the system tests the level of said signal on each chain, sequentially. The "0" compensation circuit CR (FIG. 2) is permanently operated in order to bring back the output signal to 0, but with a time constant "t". The resulting circuit corresponds to a high pass filter with a "t" time constant. The value of "t" is chosen so as to meet the standards in force relating to the ECG signal pass-band. On the other hand, this constant can change when there are great variations of the basic lines (due to the movements of the patient for example), in order to bring back the signal level around "0" more rapidly. An R-ECG resistor causes the current to flow in one of the branches of the signal generator. Said current allows the system identifying the ECG cord.

(b) For the breathing, the circuit is identical to the preceding one but the RC networks are chosen so as to have a stronger current flowing: the demodulated signal is stronger and can be analyzed by the system. A resistor, different to the R-ECG, allows the system identifying the ECG/breathing cord.

Figure 4:
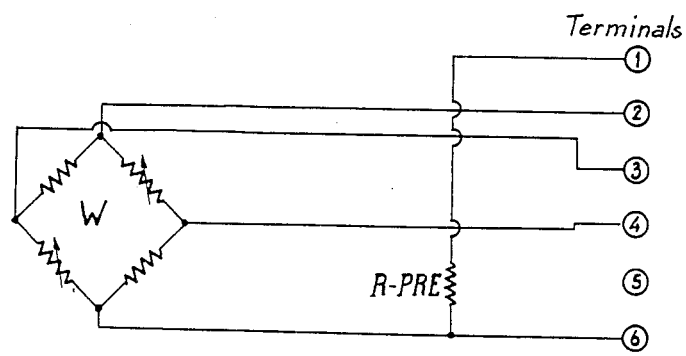
FIG. 4 shows a blood-pressure sensor.

(c) For the blood-pressure (FIG. 4), one of the square signals feeds the Wheatstone bridge W, the ground providing the reference. The two middle points of the bridge are connected to the amplifier input (A in FIG. 2). The amplified signal is demodulated. The "0" level is correctly adjusted by using the "0" compensation circuit ($C_R$ in FIG. 2). The post-amplifier ($A_p$, FIG. 2) brings the signal to an exploitable level. The R-PRE resistor identifies the sensor, as previously described. This resistor can be advantageously adjustable, so as to allow an automatic setting of the gain of the amplification chain. Indeed, the blood-pressure sensors do not always have a gain sufficiently accurate and it is very interesting to correct the gain deviations of each sensor with respect to a reference sensor. By adjusting the R-PRE resistor in a well established range, the system calculates the gain of the amplifying chain from its value by using a simple algorithm. This gain adjustment principle by the identification means can also apply to any other identification means (and to other sensors).

(d) Other sensors:

All the other sensors operate on the same principle as a Wheatstone bridge and are therefore connected in the same way as in the preceding example. The identification resistors are the only ones to be changed, in order to put the system in a position to select the correct gains, functions, processing and display.

Figure 5:
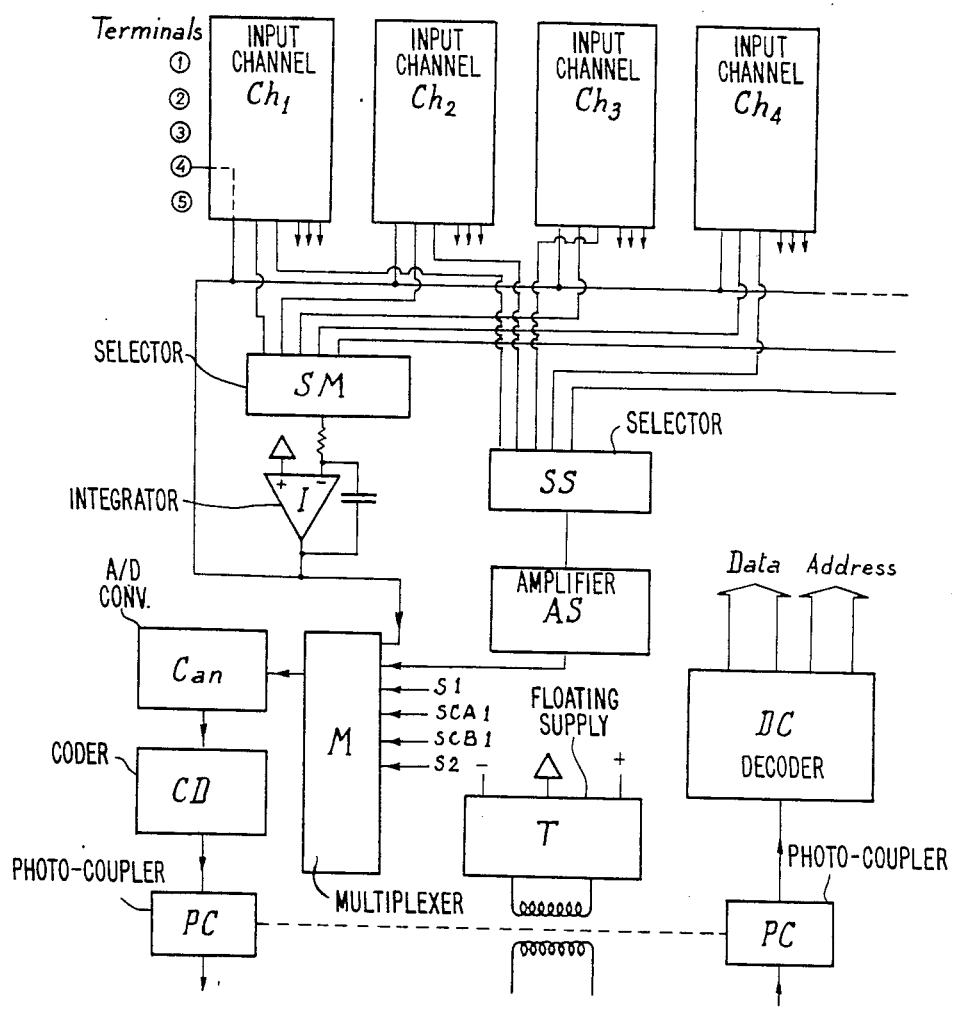
FIG. 5 shows an embodiment of an insulation and transmission circuit used in combination with the interface according to the invention.

II—Insulation and transmission circuit (FIG. 5)

The part played by this circuit consists in:
providing the "active ground" function which is necessary for a good reception of the ECG signal;
selecting the demodulated signal of the ECG or ECG-breathing chains, in order to detect either a lifting of the electrode, or the trans-thoracic impedance;
providing the transfer of the information in both directions, via an insulation circuit.

The active ground is provided by feeding an integrator I from the middle point of the differential amplifier used for the ECG. A selector of middle point SM, controlled by the system, receives all the middle points and selects the good one. The integrator output feeds all the pins "5" of the universal terminals. A single one is used to be sent back to the patient.

The demodulated signal of each input channel $Ch_1$ . . . $Ch_4$ can be read by using a selector SS and an amplifier AS. It allows the system knowing the state of each chain used for a simple ECG mode or for an ECG+-breathing mode. In the simple ECG mode, it can therefore detect a high level corresponding to the lifting of an electrode. In the ECG+breathing mode, it detects simultaneously the lifting of an electrode and the breathing signal.

A transfer of information is provided in a standard manner by using a coder CD and a decoder DC of "series" signals flowing through photo-couplers PC. The analog signals are processed in the multiplexer M, then set in a digital form by an analog to digital converter Can and finally sent to the series coder CD. The control signals are sent back on a data and address "BUS" in order to easily control all the stages of each chain and the elements of the common circuit.

A "floating" supply T completes the device.

III—Logic functions

All the logic functions will not be described here in detail, but only a general idea outile will be given on the manner the system manages the whole interface.

In the first place, the system detects the presence of sensors and establishes the state of the various chains. It deducts therefrom the gain controls and others for each chain used. On the other hand, it selects its detection system for the lifting of an electrode (or of the breathing signal). Due to a control from the operator, it can effect an "0" setting of a blood-pressure sensor. For the signals which should not include continuous components (ECG, pulse), it effects regularly the filtering functions by correcting the values of the zero compensation circuit.

The signals of each chain are processed, possibly filtered by a digital route and sent back to digital to analog converters, so that the operator can use them. The signals and the results of the processing are applied to a visualization system. Finally, in the case of a supervision system, some vital values (heart frequency, blood-pressure) are compared to thresholds in order to warn the personnel when an anomaly appears (alarms).

Amongst the advantages afforded by the device of the invention, one can mention in particular:
a systematic integration of all the equivalent functions to the various modules;
an investment by the user limited to the acquisitions unit and the sensors, while authorizing an intensive use of the devices;
a simple mechanical system, identical to that of the compact systems, therefore relatively economic;
connections reduced to the minimum;
a simplified use.

Obviously, the present invention is not limited to the embodiment and mode of application herein described, and it encompasses all possible alternatives.

What I claim is:

1. An electronic device providing a universal interface between sensors and an acquisition and processing system of the signals originating from the sensors, wherein the various sensors are connected to standardized terminals, appearing all identical to the user and comprising energization and amplifying elements, capable of being adapted to said sensors, and identification means for automatically recognizing the sensor present in the terminal, so as to allow for programming of the signal amplification, energization and processing elements.

2. A device according to claim 1, wherein said identification means is a component integrated into the sensors.

3. A device according to claim 2, wherein said identification means is a resistor, the value of said resistor being measured by the device, each type of sensor being coded by a given resistance value.

4. A device according to claim 1, wherein said identification means of the sensor is adjustable so as to provide an automatic setting of the signal amplification gain.

5. A device according to claim 1, wherein the energization elements of the sensor are associated with identification means of the sensor and are connected to the same terminals to which the sensor is connected.

6. A device according to claim 1, wherein the energization elements generate two periodical signals, in opposition to phase, said energization elements being associated with identification means, via at least one measuring circuit of the current flowing between a signal generating circuit and a pin of a terminal connecting it to the sensor.

7. A device according to claim 1, wherein the amplification elements comprise, a programmable differential amplifier, the inputs of which are connected to the active points of the sensor, a switchable demodulator connected to the output of the programmable amplifier, a circuit adapted for shifting the "0" of the signal originating from programmable differential amplifier or from the switchable demodulator, a programmable amplifier fed by the "0" shifting circuit.

8. A device according to claim 1, wherein the amplification elements comprise, in a version using a processor, a programmable differential amplifier the inputs of which are connected to the active points of the sensor, an analog to digital converter for receiving output signals from the programmable amplifier, and logical modules for controlling switchable demodulation and "0" resetting functions of said elements.

9. A device according to claim 1, wherein the signal processing system is connected in an insulated way to a plurality of input channels so as to measure the signals exiting therefrom, and also the signal exiting from the demodulator and the signal corresponding to the middle point of the programmable differential amplifier, the latter being applied to an inverting integrator the output of which supplies one of the pins of the universal terminal, a single one of said pins being used for sending back the signal on the sensor.

10. A device according to claim 1, wherein said device is disposed as a universal interface between medical sensors, such as a sensor of electrocardiographic signals, pulse, breathing, temperature, blood-pressure sensors, and an acquisition and processing unit of the signals from said sensors, such as a bedside monitor of a catheter sounding bay.

* * * * *